United States Patent [19]

Yamane et al.

[11] Patent Number: 4,469,790

[45] Date of Patent: Sep. 4, 1984

[54] CONTINUOUS AND SPONTANEOUS INTERFERON PRODUCING LYMPHOBLASTOID CELL LINES, PROCESS FOR PREPARING THE SAME, AND PROCESS FOR THE HUMAN INTERFERON PRODUCTION BY THE SAME

[75] Inventors: Isao Yamane; Takeshi Sato; Toshio Kudo, all of Sendai; Yoshiki Minamoto, Yokohama; Takehiko Tachibana, Sendai, all of Japan

[73] Assignee: Ajinomoto Co., Inc., Tokyo, Japan

[21] Appl. No.: 303,517

[22] Filed: Sep. 18, 1981

[30] Foreign Application Priority Data

Sep. 18, 1980 [JP] Japan ................. 55-129679

[51] Int. Cl.$^3$ ............ C12P 21/00; C12N 15/00; C12N 5/00; C12R 1/91
[52] U.S. Cl. .................... 435/68; 435/172.1; 435/172.3; 435/240; 435/811; 435/948
[58] Field of Search ............... 435/68, 240, 241, 811, 435/172, 948, 172.1, 172.3

[56] References Cited

U.S. PATENT DOCUMENTS 3,773,924 11/1973 Ho et al. ...................... 435/240

FOREIGN PATENT DOCUMENTS 0000520 2/1979 European Pat. Off. .

OTHER PUBLICATIONS

Friedman, *Methods in Enzymology*, vol. LVIII, Academic Press, New York, 292–296, (1979).
Steel et al., Nature, 270:729–730, (1977).
Pickering et al., PNAS USA, 77(10):5938–5942, (Oct. 1980).
Deinhart et al., J. Nat. Cancer Inst., 39:681–683, (1967).
Northrup et al., J. Nat. Cancer Inst., 39:685–689, (1967).
Kasel et al., Proc. Soc. Exp. Biol. Med., 128:351–353, (1968).
Zajac et al., Cancer Research, 29:1467–1475, (1969).
Haase et al., Proc. Soc. Exp. Biol. Med., 133:1076–1083, (1970).
Adams et al., J. Gen. Virol., 28:219–223, (1975).
Finter (Ed.), Interferon and Interferon Inducers, pp. 78, 80, 424 and 427, North–Holland Publ. Co., Amsterdam, Netherlands, (1973).
Chem. Abstracts, 89:21334n, (1978).
Chem. Abstracts, 92:126781y, (1980).

*Primary Examiner*—Esther M. Kepplinger
*Attorney, Agent, or Firm*—Oblon, Fisher, Spivak, McClelland & Maier

[57] ABSTRACT

Process for preparing a continuous and spontaneous human-interferon-producing lymphoblastoid cell line which involves (a) transforming human lymphocytes isolated from a human infant from birth up to about 2 years or an aborted human fetus, the transforming being carried out with Epstein Barr Virus and (b) selecting from the resulting transformed cell lines a cell line producing more than 1000 units of interferon per milliliter when cultivated at a cell density of $10^6$ cells per milliliter in the absence of any interferon inducer.

2 Claims, No Drawings

CONTINUOUS AND SPONTANEOUS INTERFERON PRODUCING LYMPHOBLASTOID CELL LINES, PROCESS FOR PREPARING THE SAME, AND PROCESS FOR THE HUMAN INTERFERON PRODUCTION BY THE SAME

This invention relates to (A) a process for preparing continuous and spontaneous human interferon producing lymphoblastoid cell lines named UMCL by the inventors (referred to as UNCL in the original specification of the corresponding Japanese patent application No. 129679/1980 filed on Sept. 18, 1980) which comprises (a) isolating spontaneous interferon producing lymphocytes from (i) human blood of an infant not more than about two years old, a newborn infant or an aborted human fetus, including human umbilical cord blood of a newborn infant or an aborted human fetus, or (ii) spleen cells of an aborted human fetus and (b) establishing lymphoblastoid cell lines derived from the lymphocytes by the transformation with Epstein Barr Virus (abbreviated as EBV hereinafter), said cell lines being capable of producing human interferon in high titer spontaneously and continuously, (B) an UMCL per se, i.e., a continuous and spontaneous human interferon producing lymphoblastoid cell line, and (C) a process for producing human interferon in high titer continuously with the use of UMCL cell lines but without any induction with an interferon inducer such as virus.

An interferon (abbreviated as IFN hereinafter) is known to have a potential activity as preventive drug or drug for medical treatment against virus infected diseases or virus-induced or virus-non-induced neoplastic diseases. For these purposes, however, a lot of IFN is necessary and, at the same time, the IFN has to be produced by human cells because of its species specificity, i.e., human IFN is only effective on human beings, while other mammalian IFN has no affect on human beings. Mass production of human IFN, however, has been very difficult to carry out, and an application of human IFN for medical treatment has also been limited to narrow ranges.

So far, several methods of the production of IFN are known, for example, the in vitro cultivation of (1) leucocytes isolated from adult fresh blood, (2) fibroblast cells derived from a human fetus and (3) Burkitt's lymphoma or other lymphoblastoid cell lines established from leukemic patients, and the in vivo cultivation of these neoplastic cell lines in mammals. All of these methods, however, require the essential step of adding an IFN inducer for the production of IFN in large amounts. In other words, IFN is produced only in limited periods after stimutating IFN-producing cells with a lot of an IFN inducer, such as virus, and IFN-producing cells are employed only one time. In addition, during the steps for the purification of IFN, the components derived from virus preparation including virus and egg proteins have to be completely removed or to be made completely harmless. The purification and isolation process of IFN, therefore, will be complicated. On the other hand, several spontaneous IFN-producing cell lines have been known, but their IFN productivities are quite low.

The inventors have tried to obtain potentially and spontaneously IFN producing cell lines without adding any IFN inducer and found that lymphocytes derived from a human infant not more than about two years old, a human newborn infant and a human fetus are able to produce IFN without adding any IFN inducer. These lymphocytes, however, are not able to proliferate. As the results of the further investigation, the inventors were successful in establishing lymphoblastoid cell lines from these lymphocytes through the transformation with EBV, which cell lines continuously proliferate, and in producing IFN in high titer without using any IFN inducer. These spontaneously and continuously IFN-producing lymphoblastoid cell lines were named "UMCL cell lines". These continuous and spontaneous IFN-producing lymphoblastoid cell lines can be derived only from human fetal and infant lymphocytes but not from adult peripheral blood lymphocytes, for example.

In addition, it was observed that the higher IFN productivity of lymphocytes before the EBV transformation causes the higher IFN productivity of lymphoblastoid cell lines derived therefrom with the EBV transformation and that, in the culture fluids of lymphoblastoid cell lines transplanted for two months after the transformation with EBV, no infectious EBV is detected and at the same time no EBV particles are detected inside or outside the cells by electromicroscope. From these observations, spontaneous and continuous IFN productivity seems to be derived and amplified from the latent IFN producing ability of the lymphocytes but not to be elicited by continuous infection of EBV.

In this invention, spontaneous and potent IFN-producing cell lines, UMCL cells, are established by transforming human umbilical cord blood lymphocytes, human peripheral blood lymphocytes from an infant not more than about two years old, a newborn infant or an artificially or non-artificially aborted human fetus, or splenic lymphocytes of an artificially or non-articially aborted human fetus.

These lymphocytes are easily isolated by the density gradient method employing gelatin or Ficoll isopaque. Other methods for the isolation of lymphocytes are also available. The method employing gelatin is as follows: 3 volumes of fresh heparinized blood and 1 volume of gelatin solution (3 w/v %) dissolved in phosphate buffer saline are mixed in a test tube and incubated at 37° C. for 30 min. Then the clear top layer out of the 3 layers settled is taken out, and the lymphocytes are harvested and washed by centrifugation to remove gelatin.

Lymphocyte's preparation by the Ficoll isopaque density gradient method is, for example, as follows; 1 volume of fresh heparinized blood is mixed with the same volume of equilibrated salt solution, and the mixture is layered on 1.5% Ficoll-isopaque solution (Pharmacia Fine Chemicals Co., Inc.) in a centrifuge tube. After centrifugation for 30 min. at $400 \times g$, the lymphocytes in the middle layer are taken out and washed 2 or 3 times with the same salt solution.

Splenic lymphocytes are isolated, for example, by slicing spleen and suspending the sliced spleen in saline buffer, whereby the lymphocytes are moved from the sliced spleen into the saline buffer. From the saline buffer are collected the lymphocytes in the same manner where lymphocytes are collected from blood, as just explained. Or, the saline buffer is simply subjected to centrifugation to obtain the cell fraction including the lymphocytes.

EBV employed according to this invention is easily isolated, for example, from the culture supernatant by centrifugation for 5~15 minutes at 1000–2000 rpm from a culture medium of marmoset lymphoblastoid like B-95-8 cells or human leukemic cells, QIMR-WIL, either cells being infected with EBV (J. H. Pope et al., Int. J. Cancer, 3, 857(1968), G. Miller et al., J. Viral., 18, 1071(1976), or from other cells with other methods.

For the transformation of lymphocytes with EBV, lymphocytes obtained as mentioned above from a human fetus or infant are suspended at a cell density of $5 \times 10^5 \sim 5 \times 10^6$/ml in a medium for mammalian cell culture including $5 \sim 15$ v/v% of fetal calf serum, and EBV is added to this lymphocyte suspension at a viral activity of $10^4 \sim 10^6$ TD$_{50}$/ml. After incubation at 36°-37° C. for 2-5 hrs in a humidified atmosphere containing $3 \sim 6$ v/v% CO$_2$, the lymphocytes are harvested and washed 2-3 times by centrifugation to remove the excess virus, and then resuspended at a cell density of $5 \times 10^5 \sim 5 \times 10^6$/ml in a cell culture medium containing $5 \sim 20$ v/v% fetal calf serum, followed by incubation at 36°-37° C. in a humidified atmosphere containing $3 \sim 6$ v/v% CO$_2$. Under these conditions, lymphocytes are cultured in vitro for $1 \sim 2$ months, and then lymphoblastoid cells, UMCL cells, are easily obtained by this transformation procedure. Other similar methods with EBV is also available. One unit of TD$_{50}$ is defined as a viral activity by which transforming activity of EBV is 50% in its probability where stepwise diluted virus solution is inoculated to a lymphocyte solution.

Spontaneously and continuously IFN producing lymphoblastoid cell lines, UMCL cell lines, may be immediately employed for IFN production under the above cenditions, or lymphoblastoid cells thus obtained are stored below 80° C., if necessary, after harvesting by centrifugation from the culture medium and resuspending the cells at a cell density of $10^6$-$10^8$/ml in a culture medium containing $5 \sim 15$ v/v% fetal calf serum or newborn calf serum together with 10-15 v/v% DMSO (Dimenthyl sulfoxide) or glycerine.

Spontaneous IFN producing lymphoblastoid UMCL cell lines employed in this invention are characterized as follows; (1) The cells produce IFN without IFN induction, (2) IFN productivity may be more than 1000 units per milliliter at a cell density of $10^6$ cells per milliliter in $2 \sim 4$ days under the above culture conditions, (3) Doubling time of the cell lines is $24 \sim 48$ hours under the above culture conditions, (4) The cell lines are EBV nuclear antigen (EBNA)-positive but no EBV is detected in the culture fluids and also inside the cell by electron-microscope and by EBV infection experiment, (5) The content of IgM or IgD out of the immunoglobulin distributed on the surface of the cells is more than 20% and the amount of IgM is more than 50% of the total immunoglobulin produced in the culture medium after cultivation of the cell lines, and (6) The chromosome mode number of the cell lines is 44-48.

The production of IFN according to this invention is carried out as follows; Continuous and spontaneous IFN-producing UMCL cells are inoculated in a mammalian culture medium at a cell density of $10^5 \sim 10^6$ cells/ml and cultured at 35°-38° C. for $3 \sim 6$ days under the mild stirring condition with supplying or bubbling sterilized air containing $3 \sim 6$ v/v% CO$_2$ at pH 6.0-7.5. After cultivation mentioned above, the culture medium is subjected to centrifugation, and the cells harvested are resuspended in a fresh medium at a cell density of $10^5 \sim 10^6$ cells/ml, followed by repeating the cultivation. The IFN produced in the supernatant, on the other hand, is isolated and purified as mentioned below.

The culture medium for the production of IFN according to this invention is not limited, as far as a culture medium for a mammalian cell culture is employed; for example, culture media containing 0.1-15 v/v% fetal calf serum or calf serum are preferably employed. In this invention, Eagle's MEM, RPMI 1640 or Dulbecco's Modified MEM medium containing the above serum are available. So are known serum-free media.

For the production of IFN in high titer, a metabolic inhibitor such as actinomycin D, cyclohexamide or 5-bromouracil, or a metabolic controller such as hydrocortisone prostaglandins, butyric acid or dibutyl-3'-5'-cyclic AMP is preferably added. At the same time the concentration of serum or serum albumin is appropriately controlled and culture temperature, pH, or redox-potential is optimized.

For the isolation and purification of the IFN produced in the culture medium, the following known procedures are available; for example, IFN is concentrated by salt precipitation, ultrafiltration, dialysis, centrifugation or freeze drying and highly purified by ion-exchange chromatography, gel-filtration, affinity chromatography, electroforcasing or electrophoresis, or a combination of the above procedures. The IFN produced according to this invention is characterized as follows; (1) It is stable after incubating at 56° C. for 1 hr or after keeping at pH 2 and 4° C. for 24 hrs. (2) It does not sediment after centrifuging at 100,000 xg for 1 hr. (3) Little IFN activity is detected in terms of anti-virus activity after treating with trypsin or human anti-leukocyte IFN antibody and (4) It has a major peak molecular weight of $2.1 \sim 2.5 \times 10^4$ by gel-permeation chromatography. These physico-chemical and biological characteristics of IFN are almost the same as that of human leukocyte IFN and, therefore, the IFN produced and purified according to this invention is one of human leukocyte IFNs.

The growth rate of spontaneously and continuously IFN-producing lymphoblastoid UMCL cell lines is almost the same as that of general cells derived from human beings, and UMCL cell lines are easily maintained by transplanting in every $3 \sim 6$ days, and long time culture is possible for more than one year in terms of proliferation and their IFN productivity.

For the IFN production according to this invention, UMCL cell lines are continuously cultured, for example, by culturing them in a spinner type culture vessel while new medium is being fed and, at the same time, the culture medium containing the IFN produced in adequate ratio is being taken out at an appropriate intervals. During the course of this culture IFN production is continuously and logarithmically increased. In other words, this invention provides a new practical method for the continuous mass production of IFN and this method is superior to prior art ordinary methods whereby IFN producing cells are available just one time in a batch system as far as IFN inducer is added.

This invention will be described in greater detail in the following examples, where IFN titer is determined by the semimicroassay method based on the inhibition of cytopathic effect of vesicular stomatitis virus to FL cells derived from human amnion.

LYMPHOBLASTOID CELL LINE FORMATION AND CULTURE

Example 1

Fresh heparinized umbilical cord blood was obtained from a newborn infant. Then cord blood lymphocytes were quickly isolated by the Ficoll isopaque density gradient method. The cord blood lymphocyte fraction was mixed with 3 times the volume of Eagle's Minimum Essential medium (Nissui Pharmaceutical Co.), and the mixture was centrifuged. The supernatant was discarded. After repeating this treatment 3 times, the washed lymphocytes were suspended at a cell density of $3 \times 10^6$/ml in PPMI-1640 medium (Nissui-Pharmaceutical Co.) containing 10 v/v% fetal calf serum. To this lymphocytes suspension, EBV grown in B-95-8 cells was added in a concentration of $5 \times 10^5$ TD$_{50}$/ml, and this mixture was incubated for 2 hrs at 37° C., followed by harvesting the lymphocytes with centrifuge. After washing these lymphocytes with Eagle's MEM medium 3 times, the lymphocytes were resuspended at a cell density of $3 \times 10^6$/ml in RPMI-1640 medium containing 10 v/v% fetal calf serum and cultured at 36°~37° C. for 1.5 months in a humidified atmosphere containing 5% $CO_2$ in air. During this cultivation, fresh RPMI-1640 medium containing 10 v/v% fetal calf serum was added in an equal volume or half volume of culture medium was exchanged with this fresh medium in every 5 days.

Lymphoblastoid cells were prepared from 9 umbilical cord bloods and from 7 adult peripheral bloods and the IFN productivity of these transformed cells was assayed. The assay was carried out as follows; each lymphoblastoid cell line sample was cultured at an initial cell density of $5 \times 10^5$/ml in RPMI-1640 medium containing 10 v/v% fetal calf serum at 37° C. for 5 days in a humidified atmosphere of 5% $CO_2$ in air and IFN activity in the culture supernatant was determined. The results are listed in Table 1.

TABLE 1

| | Cell line samples | IFN activity ($\times 10^3$ U/ml) |
|---|---|---|
| Umbilical cord blood lymphoblastoid cell lines | UMCL-1 | 2.5 |
| | UMCL-2 | 6.1 |
| | UMCL-3 | 4.5 |
| | UMCL-4 | 1.2 |
| | UMCL-5 | 8.5 |
| | UMCL-6 | 5.1 |
| | UMCL-7 | 3.0 |
| | UMCL-8 | 15.3 |
| | UMCL-9 | 4.2 |
| Adult peripheral blood lymphoblastoid cell lines | SA | <0.1 |
| | KN | 0.2 |
| | SU | <0.1 |
| | MI | <0.1 |
| | UE | 0.3 |
| | KU | <0.1 |
| | FU | <0.1 |

Example 2

Spleen was taken out from aborted fetuses (15~20 week's old) and sliced with a surgical knife into 1 mm pieces. The splenic cells harvested were washed 2 times with 10 ml of Hank's buffer solution, and the splenic lymphocytes were isolated with the Ficoll-isopaque density gradient method. The splenic lymphocytes were transformed with EBV in the same way as mentioned in Example 1 in connection with umbilical cord blood lymphocytes. Two cell line samples were obtained. The IFN productivity was assayed as described in Example 1 except that the initial cell density and culture period were varied as mentioned in Table 2.

TABLE 2

| Cell line sample | Initial cell density | Culture period | IFN activity |
|---|---|---|---|
| UMCL-S-1 | $5 \times 10^5$/ml | 4 days | $6.8 \times 10^3$ U/ml |
| UMCL-S-2 | $1 \times 10^6$/ml | 2 | $1.3 \times 10^4$ U/ml |

Example 3

Fresh heparinized peripheral bloods were obtained from infants of various monthly ages. Then the lymphocytes fraction was isolated with the gelatin method and washed 3 times with Eagle's MEM. The peripheral lymphocytes were transformed and cultured in the same manner where the umbilical cord blood lymphocytes mentioned in Example 1 were treated.

IFN activities in the cultured media of the transformed infant peripheral lymphocytes were assayed as described in Example 1. The results are shown in Table 3.

TABLE 3

| Cell line No. | age (months old) | IFN activity ($\times 10^3$ U/ml) |
|---|---|---|
| UMCL-10 | 2 | 12.5 |
| UMCL-11 | 4 | 15.8 |
| UMCL-12 | 6 | 10.1 |
| UMCL-13 | 15 | 5.1 |

PRODUCTION OF IFN

Example 4

The UMCL-3 cell line was inoculated at a initial cell density of $5 \times 10^5$/ml in a culture bottle containing RPMI-1640 medium supplemented with 10 v/v% fetal calf serum. Under the condition of a humidified 5% $CO_2$-containing air, this cell line was cultured at 36°–37° C. for 5 days. Then the UMCL-Cells were harvested by centrifugation at 1000 rpm for 10 min. and resuspended in the same fresh medium at the same initial cell density ($5 \times 10^5$/ml) as above.

This procedure was repeated 5 times. The culture supernatants obtained at the respective steps were assayed for IFN titer. Results are shown in Table 4.

TABLE 4

| Step | Volume of supernatant | IFN activity | Total IFN produced |
|---|---|---|---|
| 1 | 9 ml | $3.5 \times 10^3$ U/ml | $3.2 \times 10^4$ U |
| 2 | 35 | 4.8 | $1.7 \times 10^5$ |
| 3 | 150 | 4.0 | $6.0 \times 10^5$ |
| 4 | 520 | 5.1 | $2.6 \times 10^6$ |
| 5 | 1650 | 4.2 | $6.9 \times 10^6$ |

Example 5

UMCL-6 cells were inoculated at a cell density of $5 \times 10^5$/ml in 1000 ml Dulbecco's modified MEM (Nissiu Pharmaceutical Co.) containing 5 v/v% fetal calf serum in a glass jar fermentor of 3 l capacity. The cells were cultured at 37° C. for 4 days by continuously feeding sterilized 5 v/v% $CO_2$-containing air at a rate of 300 ml/min and agitating with a spinner at 30–100 rpm. The first batch culture was finished by stopping agitation and aeration and the culture mass was allowed to stand for 3 hrs to settle down the cells. The culture supernatant (800 ml) was taken out by suction and centrifuged immediately at 1200 rpm for 15 min. to remove the contaminant cells. Then 1800 ml of the same fresh medium as mentioned above were fed, followed by carrying out the 2nd batch culture for 3 days under the same conditions as above and centrifuging the 2nd batch culture at 1200 rpm for 15 min. to obtain another culture supernatant (1900 ml).

IFN titers in the 1st and 2nd batch culture supernatants were $3.9 \times 10^6$ and $1.5 \times 10^7$ unit, respectively.

Example 6

The same procedure as in Example 4 was repeated 4 times with the use of the UMCL-11 cell line instead of the UMCL-3 cell line. The results are shown in Table 5.

TABLE 5

| Step | Volume of supernatant (ml) | IFN activity ($\times 10^4$ U/ml) | Total IFN produced ($\times 10^5$) |
| --- | --- | --- | --- |
| 1 | 10 | 1.5 | 1.5 |
| 2 | 45 | 1.0 | 4.5 |
| 3 | 180 | 0.98 | 17 |
| 4 | 810 | 0.97 | 79 |

What is claimed is:

1. A process for preparing a continuous and spontaneous human-interferon-producing lymphoblastoid cell line, which comprises:
   transforming human lymphocytes isolated from a human infant from birth up to about 2 years, a new-born infant, or an aborted human fetus, wherein said transforming is performed with Epstein Barr Virus and wherein multiple human lymphocytes are transformed to give multiple transformed cell lines, and
   selecting a cell line from said transformed cell lines which produces more than 1000 units of interferon per milliliter when cultivated at a cell density of $10^6$ cells per milliliter in the absence of any interferon inducer.

2. A process for the production of human interferon, which comprises:
   culturing a cell line derived from a human lymphocyte isolated from a human infant from birth up to about two years, a new-born infant, or an aborted human fetus that has been transformed with Epstein Barr Virus, wherein said culturing occurs in the absence of any interferon inducer and said cell line produces more than 1000 units of interferon per milliliter when cultivated at a cell density of $10^6$ cells per milliliter, and
   isolating human interferon from said culture medium.

* * * * *